United States Patent [19]

Rossi et al.

[11] Patent Number: 5,144,019

[45] Date of Patent: Sep. 1, 1992

[54] RIBOZYME CLEAVAGE OF HIV-I RNA

[75] Inventors: John J. Rossi, Glendora; Edouard M. Cantin, Los Angeles; John A. Zaia, Arcadia; Pairoj Chang, San Dimas, all of Calif.

[73] Assignee: City of Hope, Duarte, Calif.

[21] Appl. No.: 369,489

[22] Filed: Jun. 21, 1989

[51] Int. Cl.$^5$ .................... C07H 17/00; A61K 37/54
[52] U.S. Cl. .................................. 536/27; 424/94.6; 514/934
[58] Field of Search .............. 424/94.6; 536/27; 514/44, 934

[56] References Cited

PUBLICATIONS

J. Perreault, et al., Nature, 344:565–567, 1990.
Chem. Abst. 110(21):187321k, 1989; 112(7):51284; 1990; 112(7):52942j, 1990; 112(13):1135276, 1990.
Chem. Abstract, 112(19):175480q, 1990.
F. Cameron, et al PNAS, 86:9139–9143, 1989.

*Primary Examiner*—John W. Rollins
*Attorney, Agent, or Firm*—Edward S. Irons

[57] ABSTRACT

Stable, catalytic efficient ribozymes useful, inter alia, to cleave HIV-I RNA or any other viral or endogenous cellular RNA, in vitro and in vivo, cells transformed with such ribozymes and the use of such ribozymes and cells for anti-AIDs therapy are disclosed.

3 Claims, 6 Drawing Sheets

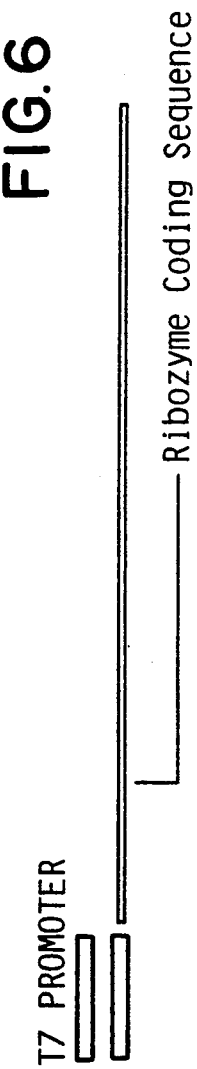

RIBOZYME CLEAVAGE OF HIV-I RNA

This invention was made with government support under Grant No. J. R. NIAID R01 AI29329 awarded by the National Institutes of Health. The government has certain rights in the invention.

FIELD OF THE INVENTION

This inventions relates to ribozymes effective to cleave HIV-I RNA. More particularly, the invention relates to cells transformed with such ribozymes, and to anti-AIDS therapy including the administration of such ribozymes to mammalian patients including humans.

BACKGROUND OF THE INVENTION

One form of gene expression impairment by RNA-RNA duplex formation has been termed "antisense" inhibition. Exploitation of antisense gene regulation could lead to potent anti-viral therapy. A serious limitation of the antisense approach, especially as it applies to anti-viral activity, is that it is stoichiometric and may require large molar excesses of anti-sense versus target RNA to be effective.

Within the last few years, discoveries of ribozymes, e.g., RNAs with enzymatic activities have led to the development of antisense molecules which not only form RNA-RNA hybrids, but catalytically cleave the covalent phosphodiester linkages and turnover large numbers of substrate molecules. Ribozymes can now be targeted to virtually any RNA transcript, and efficient cleavage can be readily achieved in vitro. See, Kim, S. H., et al. *Proc. Natl Acad. Sci. U.S.A.* 84:8788–8792 (1987); Haseloff, J., et al., *Nature* 234:585–591 (1988); Cech, T. R. *JAMA* 260:3030–3034 (1988); Jeffries, A. G., et al., *Nucleic Acids Research* 17:1371–1377 (1989).

Haseloff and Gerlack developed a set of rules useful to design transacting ribozymes. The utility of these rules was demonstrated by ribozymes effectively targeted to several different sites within the chloramphenical acetyltransferase transcript. Haseloff states that "A major potential application for these highly sequence specific endoribonucleases is in cleavage and thereby inactivation of gene transcripts in vivo . . . . Provided that the transcribed sequences of the gene are known, it should be possible to target one or more ribozymes against specific RNA transcripts. Expression in vivo of such ribozymes and cleavage of the transcripts would in effect inhibit expression of the corresponding gene. This 'auto-gene' activity of the ribozymes could provide a basis for various gene and viral therapies and analyses" (pp. 590–591).

SUMMARY OF THE INVENTION

Stable, catalytic efficient ribozymes useful, inter alia. to cleave HIV-I RNA or any other viral or endogenous cellular RNA, in vitro and in vivo, cells transformed with such ribozymes and the use of such ribozymes and cells for anti-AIDs therapy are disclosed.

DESCRIPTION OF THE FIGURES

FIG. 6 is a schematic diagram indicating the hemiduplex T-7 promoter construct used to transcribe the ribozymes illustrated by FIGS. 1 to 4 and 5.

FIG. 7 illustrates a mammalian ribozyme expression vector.

DETAILED DESCRIPTION OF THE INVENTION

Figure 1:
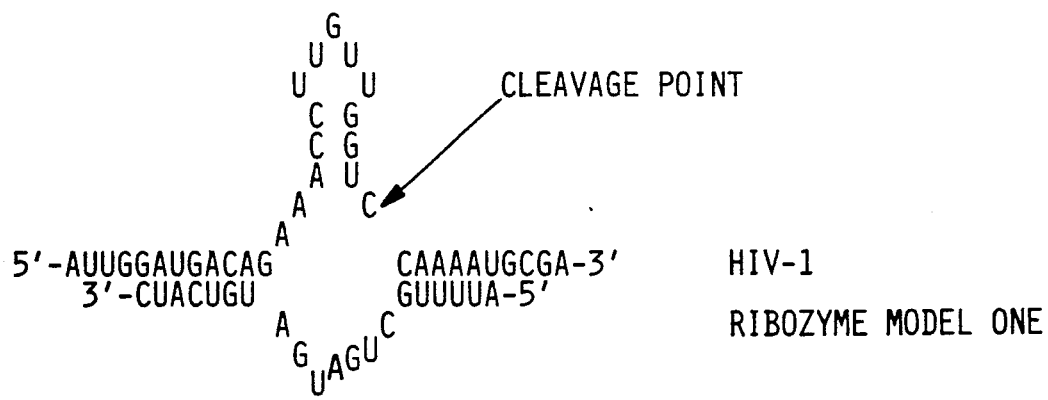
FIG. 1 illustrates a first ribozyme associated with a first cleavage point in the qaq region of HIV-I.

The mechanism of ribozyme cleavage requires highly conserved sequences that form catalytically active structures. Trans-active ribozyme structures require a target RNA strand including the cleavage site. The target strand functions as a substrate for the catalytic strand. The target or substrate strands useful in this invention include conserved sequences GAAAC $(X)_n$ GU in which X is any nucleotide and n may have any value. Preferably the value of n is from 0 to about 50.

Eleven GAAAC (X)n GU substrate units in HIV-I HXB-2 isolate, see Rattner, L., et al., Nature 313:277–284 (1985) are set forth in Table I.

TABLE I

| Unit No. | Sequence | Base Coordinates |
|---|---|---|
| 1. | 5' pppGCGCC<u>GAAACA</u>CCGU<u>GUC</u>UCGAGC—OH 3'  (Cleavage Site after GUC) | |
| 2. | 5'CA<u>GAAAC</u>CUUGUUGG<u>GUC</u>CAAAAUGCGAACC 3'  (Cleavage Sites) | ?? |
| 3. | 5'AAUCCUGGCCUGUUA<u>GAAAC</u>AUCAGAAGGCU<u>GUA</u>GACAAAAUACUGGGACAGCU—3'  (Cleavage site) | |
| 4. | 2411  CAGGAACATG<u>GAAAC</u>CAAAAATGATAGGGGGAATTGGAGG<u>GTT</u>TTATCAAAGTAAGACAGT  (Cleavage Site) | |

TABLE I-continued

| Unit No. | Sequence | Base Coordinates |
|---|---|---|

5. 3768
   ATACAAAAGGAAACATGGGAAACATGGTGGACAGAGTATT
   Cleavage Sites 6. 3777
   CCCATACAAAAGGAAACATGGGAAACATGGTGGACAGAGTATTGGCAAGCC
   Cleavage sites 7. 3894
   TAGTAGGAGCAGAAACCTTCTATGTAGATGGGGCAG
   Cleavage Site 8. & 9. 4536 and 4548
   GTTATTCCAGCAGAAACAGGGCAGGAAACAGCATATTTTCTTTTAAAATTAGCAGGAAGAT
   GGCCAGTAAAAACAAT
   Cleavage Site 10. 5574
    CCTAGTGTTACGAAACTGACAGAGGATAGATGGAACAAGCCCCAGAAGACCAAGGGCCACA
    GAGGGAGCCACACAATGAAGGACACTAGAGCTTTTAGAGGAGCTTAAGAATGAAGCTGTT
    AGACATTTTCCTA
    Cleavage site 11. 5574
    G                        G
    AACATATCTATGAAACTTATGGGGATACTTGGGCAGGAGTGGAAGCCATAATAAGAATTCT
    C
    GCAACAACTGCTGTTTATCCATTTTCAGAA
    Cleavage site Preferred cleavage sites are preceeded by the trinucleotides GUC and GUU. Cleavage sites preceeded by the trinucleotide GUG are not favored.

One aspect of this invention includes predesigned, synthetic, catalytic strands specifically targeted to regions of HIV-I RNA which include such substrate units. This aspect of the invention is exemplified by synthetic catalytic strands which include the core sequence 3' YGCNGUCZ 5' in which N is any nucleotide with 3'and 5' flanking sequences Y and Z complementary to the target of at least about 5, preferably about 5 to 10, nucleotides complementary to target sequences adjacent the cleavage site.

EXAMPLE I--RIBOZYME TRANSCRIPTION

FIGS. 1–3 and 5

The schematic diagram of FIG. 6 indicates the hemiduplex T7 promoter template used to transcribe the ribozymes shown in FIGS. 1 to 3 and 5. The gag (FIGS. 1–3) or LTR (FIG. 5) template was transcribed from a T7 promoter using a cloned HIV-I DNA segment in the Bluescript (Statagene) vector system. Several picomoles of template were incubated in a 20 microliter reaction containing 500 micro molar concentrations of ATP, CTP, and GTP, 50 micromolar concentration of UTP and 10 to 20 microcuries of $^{32}$P-labelled UTP (3000 Ci/mmole) in 40 mM Tris-HCl pH 8.0, 20 mM MgCl, 10 mM NaCl, 1 mM dithiothreitol and 20 units of placental ribonuclease inhibitor. Ten units of T7 RNA polymerase were added, and transcription allowed to proceed for 30 min. to 1 hour at 37° C. The reactions were terminated by phenol extraction, followed by ethanol precipitation, and the products purified by electrophoresis in a 6% or 10%, polyacrylamide-7M urea gel. The radioactive products were eluted by diffusion in sterile H$_2$O and quantitated by counting in a scintillation counter set to monitor $^{32}$P.

Figure 4:
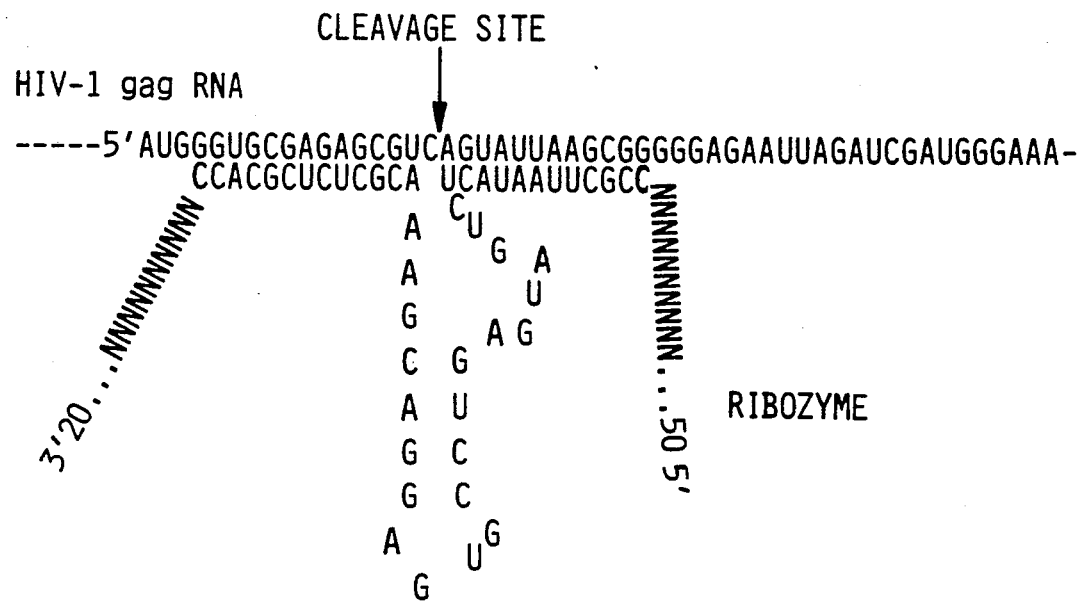
FIG. 4 illustrates a fourth ribozyme associated with yet another cleavage point in the gag region of HIV-I.

The Ribozyme of FIG. 4

The ribozyme gene depicted by FIG. 4 was first cloned into a Bluescript transcription vector and thereafter into the Bam H1 site of the mammalian expression vector depicted in FIG. 7.

More specifically, 20 picomoles of each oligonucleotide, which have 10 bases of complementary sequence at their 3' termini, are mixed together in a 50 ul reaction containing the following: 50 mM KCl, 10 mM tris-HCl pH 8.3, 1.5 mM MgCl, 0.01% (w/v) gelatin, 200 uM each dATP, and the reaction mixture is overlain with 50 ul of mineral oil. The oligonucleotides are polymerized by cycling 10 times under the following conditions: 95° C. for 2', 45° C. for 2' and 72° C. for 3'. The product was electrophoresced in an 8% polyacrylamide gel. The polyacrylamide gel, stained with ethidium bromide (1 ug/ml) and a gel slice containing the fragment cut out, and the fragment eluted by diffusion in 10 mM Tris pH 8.0, 1 mM EDTA. The eluted double stranded DNA is then restricted with the appropriate restriction endonuclease to generate cohesive termini for subsequent ligation to a similarly treated bacterial plasmid vector such as Bluescript. The fragment is ligated with the vector under standard published conditions, and transformed into E. coli cells, propagated, amplified and purified for subsequent use in in vitro transcription reactions. The Bluescript vector containing the ribozyme cloned in this manner is linearized with a restriction enzyme which cuts distal to the cloned ribozyme, and the appropriate RNA polymerase, T7 or T3, is added in a standard transcription reaction to produce the RNA ribozyme.

The resultant construct generated a ribozyme as shown in FIG. 4 with 50 non-HIV-I target 5' and 20 non-HIV targeted 3' nucleotides. The extra nucleotides were derived from the polylinker sequences of the Bluescript vector.

EXAMPLE II--RIBOZYME CLEAVAGE REACTIONS AND REACTION PRODUCTS

Figure 2:
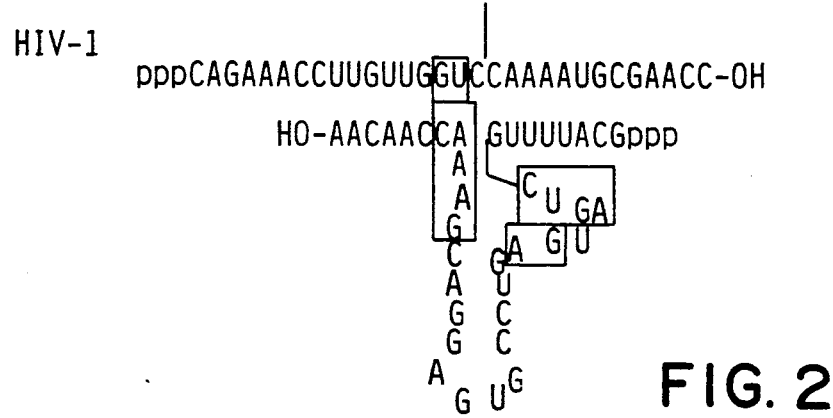
FIG. 2 illustrates the design of a second ribozyme associated with the same cleavage point in the gag region of HIV-I as shown in FIG. 1.
Figure 3:
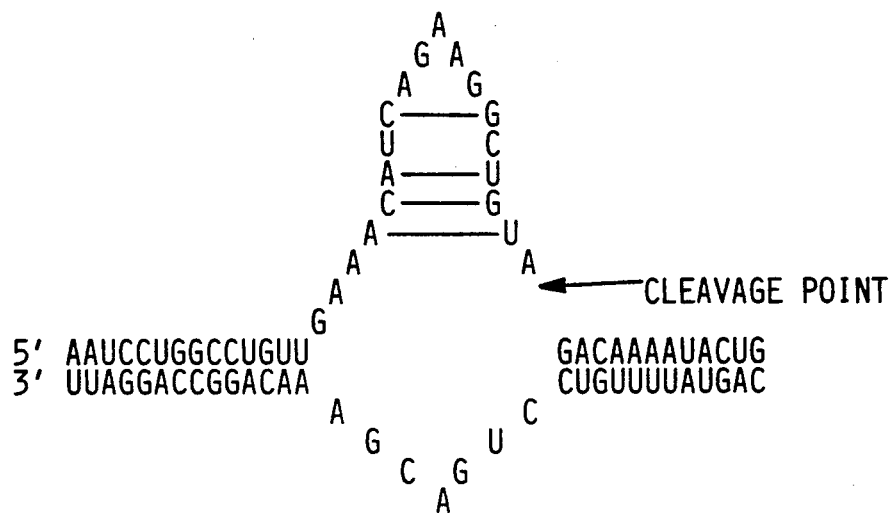
FIG. 3 illustrates the a third ribozyme associated with another cleavage point in the gag region of HIV-I.
Figure 5:
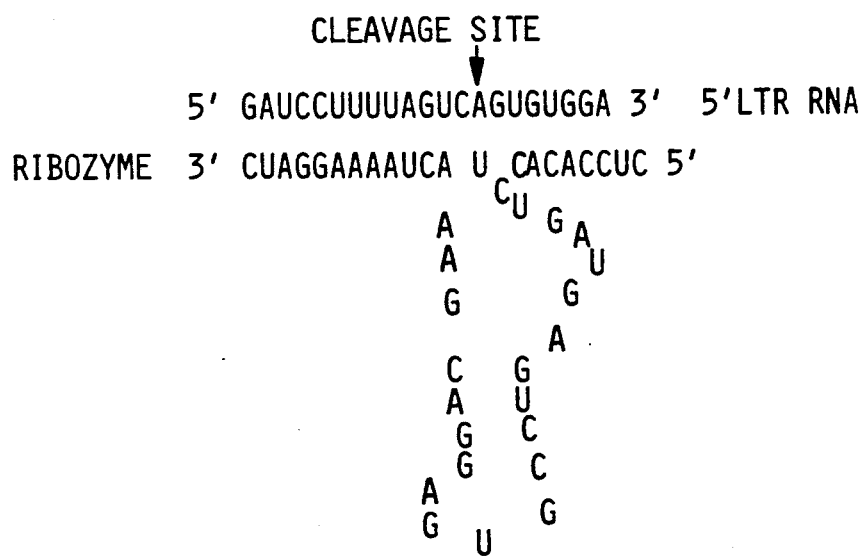
FIG. 5 illustrates a fifth ribozyme targeted to a cleavage site in the 5 LTR region of HIV-I.

Reaction conditions for the cleavage by the ribozymes of FIGS. 1, 2 and 5 were: ca. 1 pmole ribozyme and template in a 10 μl reaction containing 10 to 20 mM MgCl, 50 mM Tris-HCL pH 7.5, 1 mM EDTA. The RNA segments were heated to 90° C. briefly, quick-chilled in ice, the MgCl was added and the reactions were brought to 37° C. for 14 hours. The reactions were stopped by the addition of an equal volume of 10M urea and EDTA to 12 mM final.

The reaction mixes were electrophoresed in a denaturing polyacrylamide gel and the gel was autoradiographed.

Figure 8:
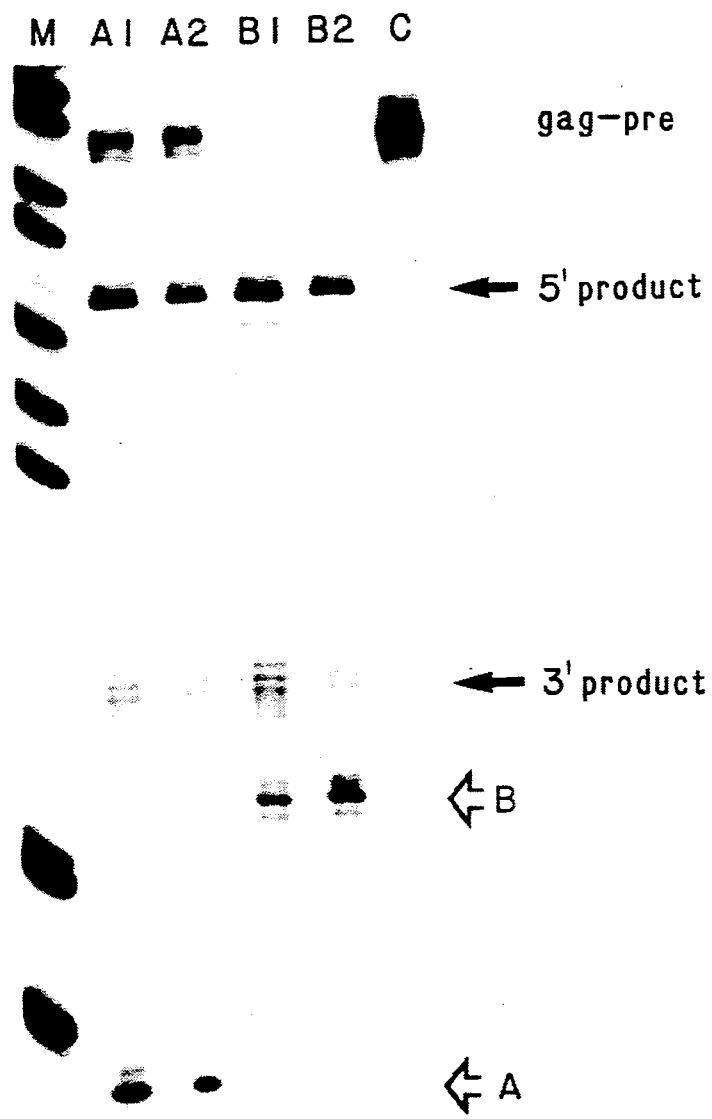
FIG. 8 is a copy of an autoradiograph which shows the HIV-I RNA cleavage reaction products formed with the ribozymes of FIGS. 1 and 2.

FIG. 8 is a copy of the autoradiograph which depicts HIV-I cleavage products formed with the ribozymes of FIGS. 1 and 2. Symbols: M, molecular weight marker, Hpa II digested pBR322 DNA; A1, ribozyme A (FIG. 1) and substrate not capped with GppppG; A2, ribozyme A and substrate capped; B1, ribozyme B (FIG. 2) and substrate not capped; B2, ribozyme B and substrate capped during in vitro transcription; substrate without added ribozyme incubated under otherwise identical conditions. The positions of the ribozymes (A and B), the substrate (gag-pre) and 5' and 3' products are indicated.

Figure 9:
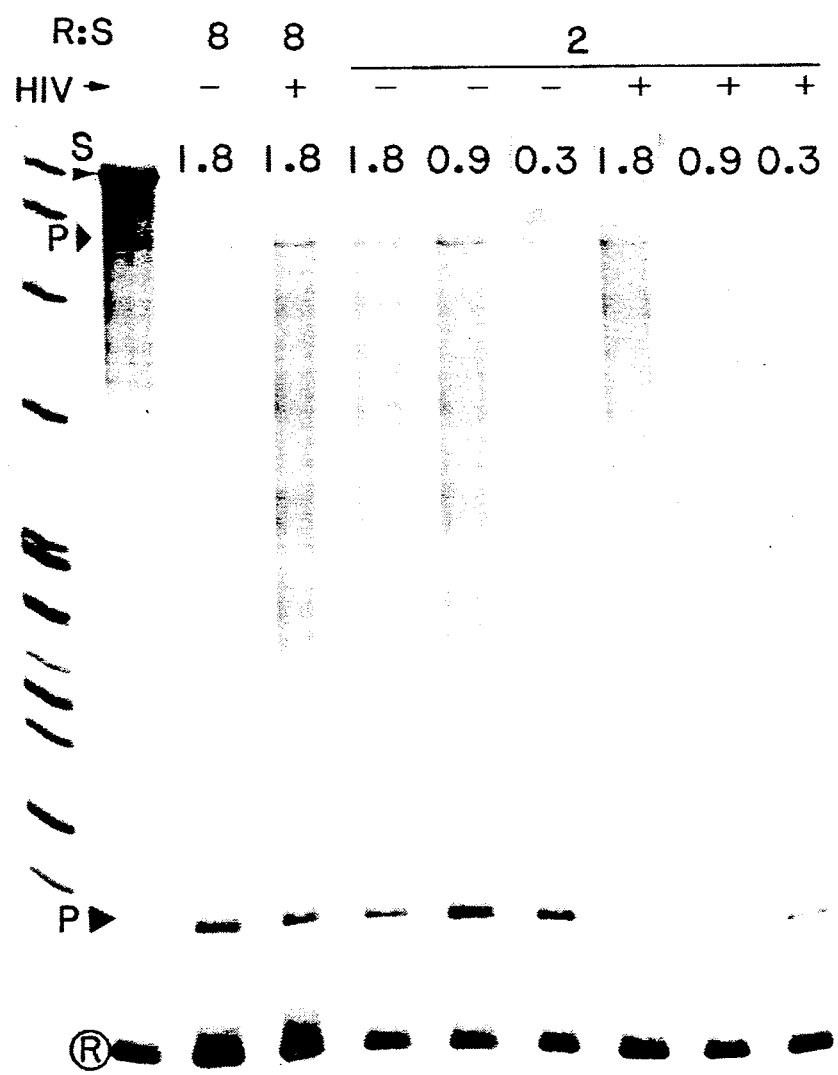
FIG. 9 is a copy of an autoradiograph of the HIV RNA cleavage reaction products formed with the ribozyme shown in FIG. 4.

FIG. 9 is a copy of an autoradiograph of the HIV RNA cleavage reaction products formed with the ribozyme shown in FIG. 4. The FIG. 4 ribozyme, in common with ribozymes which will be expressed from a promotor in a living cell, has flanking 5' and 3' sequences. To determine whether or not such flanking sequences interfere with its catalytic activities, the ribozyme of FIG. 4 was tested in vitro against a 620 nucleotide gag region substrate. In addition to the substrate, varying amounts of total RNA prepared from H9 lymphocytes which were either uninfected or infected with HIV-I, were added to the ribozyme reaction. This was done to simulate a complex in vivo milieux. Two different ratios of ribozymes to imput target RNA (R:S) were utilized as indicated by FIG. 9. More particularly, as the Figure indicates, the amounts of total RNA from either HIV-I infected or uninfected cells range from 0.3 to 1.8 μg. In the Figure, the substrate is indicated "S", the cleavage products "P" and the ribozyme "R".

It appears from the Figure that the extra flanking sequencing did not inhibit cleavage of target sequences and that increasing amounts of RNA from uninfected H9 cells had little or no effect on the cleavage reaction.

EXAMPLE III--GREATER THAN STOICHIOMETRIC SUBSTRATE CLEAVAGE

Ribozymes are distinguished from other classes of antisense RNAs by the ability to process excess molar amounts of substrate.

This example illustrates the cleavage of greater than stoichiometric amounts of substrate by the ribozymes of FIGS. 2 and 5.

In these experiments the ratios of substrate to ribozyme were varied from 1:1 to 50:1. Incubation with large molar excesses of substrate resulted in catalytic cleavage of greater than stoichiometric amounts of substrate over the 14 hour at 37° C. incubation period. Reaction conditions were otherwise the same as described with respect to FIG. 9.

Figure 10:
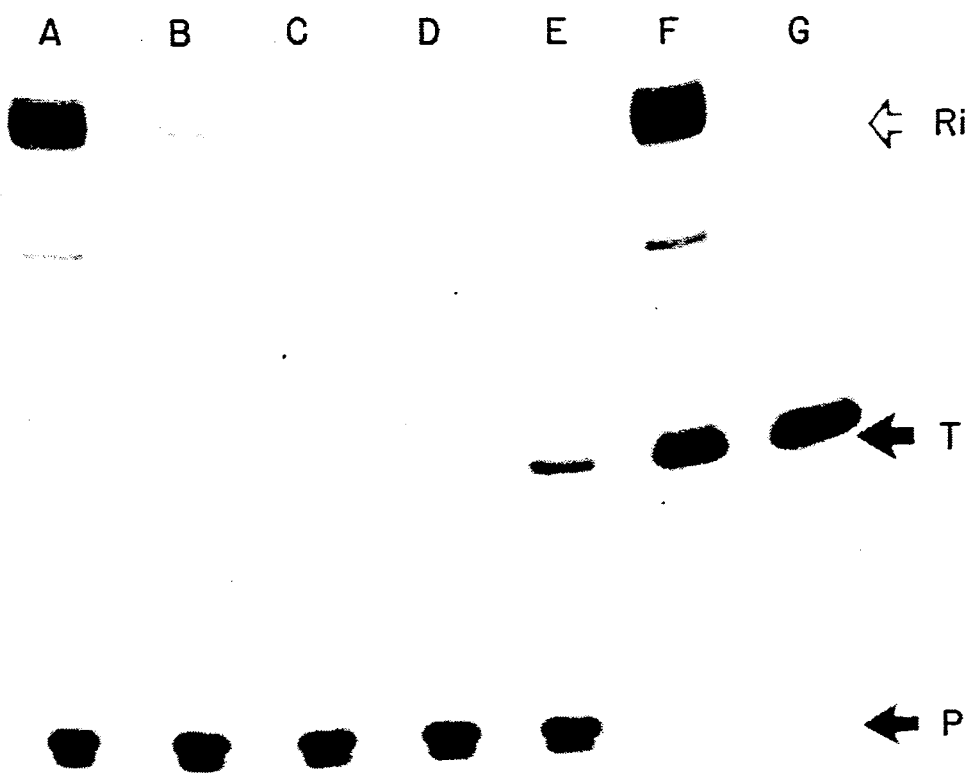
FIG. 10 is a copy of an autoradiograph which indicates substrate turnover of the ribozyme of FIG. 5.

The autoradiographs of FIGS. 10 and 11 illustrate the results obtained with the ribozymes of FIGS. 2 and 5, respectively. In each case the ribozyme was titrated relative to a fixed amount of template such that the target to ribozyme ratios were: lane A 1:1; lane B, 5:1; lane C, 10:1; lane D, 20:1; lane E, 50:1; lane F ribozyme plus substrate, no Mg++; lane G, template alone, no ribozyme, plus Mg++.

EXAMPLE IV--TRANSFECTION OF RIBOZYME INTO CD4 BEARING HeLa CELLS

Example III describes the cloning of the ribozyme of FIG. 4 into the expression vector of FIG. 7.

The cloned ribozyme was transfected into CD4+HeLa cells by calcium phosphate or lipofection techniques.

The ribozyme gene transfected into CD4+HeLa cells was assayed for expression into RNA by polymerase chain reaction (PCR) assay using primers complementary to sequences in the SV40 portion of the vector in FIG. 7, as well as a primer complementary to the 5' end of the ribozyme gene itself. The PCR amplified products were detected by a third probe complementary to the 3' region of the ribozyme gene. Several clones of transfected CD4+ cells were shown by the assays to express the ribozyme with which they have been transfected. These assays indicate that several of the clones of the CD4+HeLa cells express the ribozyme gene depicted by FIG. 4.

EXAMPLE V--BIOLOGICAL ACTIVITY

The expression product of the transfected CD4+HeLa cells described in Example IV was assed to determine the presence or absence of biological activity indicative of the presence of the ribozyme of FIG. 4 in the expression product. CD4+HeLa cells expressing the ribozyme were infected with HIV-I, and assayed on dag 7 post-infection for the HIV-I antigens. These assays involve standard immune precipitation of HIV-I encoded antigens particularly qaq and pol gene products utilizing commercially available antibodies supplied by either Hoffman-LaRoche or E. I. DuPont de Nemours corporations. Several of the ribozyme expressing clones showed large reductions in HIV-I antigens relative to non-ribozyme expressing clones.

THERAPEUTIC PROCEDURES

The therapy utilizing the ribozymes of this invention may be directed at HIV-1, HIV-2 or any viral RNA for which nucleotide sequence information is available. Therapeutic use of ribozymes to inactivate endogenous cellular sequences is also covered by this invention. This includes endogenous products such as the ras, src, myc oncogenes or any endogenous gene product which may be deleterious to the host organism. Ribozymes can be delivered to the appropriate cells utilizing targeted liposomes. This can be accomplished with either free ribozyme, or DNA encoding the ribozyme with appropriate transcriptional control signals flanking the ribozyme gene such as depicted in FIG. 7. Alternatively, ribozyme genes can be delivered to pluripotent stem cells via either cellular transfection methods (calcium phosphate, lipofection or electroporation) or via retroviral vectors. The cells are reintroduced into the patient using established methods of autologous bone marrow transplantation. The cells harboring ribozymes active against viral pathogens will have a selective advantage over non-expressing cells since the pathogens will be incapable of propagating in these cells.

I claim;

1. A snythetic catalytic RNA ribozyme strand targeted to a region of HIV-I RNA having the sequence GAAAC$(X)_n$GU in which X is any nucleotide and the value of n is from 0 to about 50, said snythetic catalytic ribozyme strand having the formula 3′ YAGNAGUCZ 5′ in which N is any nucleotide, Y and Z are flanking sequences of at least five nucleotides complementary to sequences adjacent to cleavage site in the GAAAC(X-$)_n$GU target RNA sequence.

2. A ribozyme comprising an RNA hybrid having a target strand and catalytic strand said target strand having including the sequence GAAAC$(X)_n$GU said catalytic strand inclluding the sequence 3′ YAGNAGUCZ 5′ in which N is any nucleotide and in which flanking sequences Y and Z are each sequences of at least five nucleotides complementary to sequences adjacent a dleavage site in said target strand.

3. A ribozyme construct having the formula:

* * * * *